United States Patent
Gatineau et al.

(10) Patent No.: US 11,576,692 B2
(45) Date of Patent: Feb. 14, 2023

(54) SYSTEM FOR CRUSHING AND/OR REMOVING BODY STONES, METHOD FOR PROVIDING SUCH A SYSTEM AND ADAPTER ELEMENT

(71) Applicant: FERTON HOLDING S.A., Delémont (CH)

(72) Inventors: Vincent Gatineau, St. Julien en Genevois (FR); Jean-Yves Girod, Gland (CH); Paolo Longoni, Coppet (CH); Maxime Lok, Échenevex (FR); Frederic Michaud, Morbier (FR); Gaël Nini, Lausanne (CH); Nicolas Poulat, Seynod (FR); Denis Rambaud, Geneva (CH)

(73) Assignee: FERTON HOLDING S.A., Delémont (CH)

( * ) Notice: Subject to any disclaimer, the term of this patent is extended or adjusted under 35 U.S.C. 154(b) by 148 days.

(21) Appl. No.: 16/963,441

(22) PCT Filed: Jan. 18, 2019

(86) PCT No.: PCT/EP2019/051279
§ 371 (c)(1),
(2) Date: Jul. 20, 2020

(87) PCT Pub. No.: WO2019/141821
PCT Pub. Date: Jul. 25, 2019

(65) Prior Publication Data
US 2021/0038239 A1    Feb. 11, 2021

(30) Foreign Application Priority Data
Jan. 19, 2018   (DE) .................... 10 2018 101 221.7

(51) Int. Cl.
*A61B 17/22*  (2006.01)
*A61B 90/98*  (2016.01)
*A61B 17/00*  (2006.01)

(52) U.S. Cl.
CPC ........ *A61B 17/22012* (2013.01); *A61B 90/98* (2016.02); *A61B 2017/00486* (2013.01); *A61B 2017/22025* (2013.01)

(58) Field of Classification Search
CPC .............. A61B 17/22; A61B 17/22004; A61B 17/22012; A61B 17/2202; A61B 17/225;
(Continued)

(56) References Cited

U.S. PATENT DOCUMENTS 5,992,405 A * 11/1999 Sollami ................ E21C 35/1933
                                                          125/36
2004/0138594 A1* 7/2004 Sekino ............. A61B 17/22012
                                                           601/4
(Continued)

FOREIGN PATENT DOCUMENTS

| EP | 0676175 A1 | 10/1995 |
| EP | 0947171 A2 | 10/1999 |
| EP | 1504724 A1 | 2/2005 |

OTHER PUBLICATIONS

International Search Report dated Jun. 26, 2019 re: Application No. PCT/EP2019/051279, pp. 1-3, citing: US 2007038160 A1, US2011208206 A1, US2011089248 A1, EP 0947171 A2 and EP 0676175 A1.
(Continued)

*Primary Examiner* — Robert A Lynch
(74) *Attorney, Agent, or Firm* — Cantor Colburn LLP

(57) ABSTRACT

A system for crushing and/or removing body stones, includes a source causing shock waves and/or ultrasonic waves, and a probe, wherein the source and the probe are reversibly connectable to one another via an interface for
(Continued)

transmitting the shock waves and/or ultrasonic waves to the probe. The probe includes an identification element for identifying the probe, the identification element being arranged in or on the probe in a sound-protected manner. The identification element is preferably an RFID element.

9 Claims, 7 Drawing Sheets

(58) Field of Classification Search
CPC .... A61B 17/320068; A61B 2017/0046; A61B 2017/00464; A61B 2017/0047; A61B 2017/00486; A61B 2017/22014; A61B 2017/22015; A61B 2017/22025; A61B 2017/320088; A61B 2017/992; A61B 90/98; A61B 2090/00988; A61B 2090/0803; A61B 2090/0804; A61B 2090/0805; A61B 2090/0806; A61B 2090/0814; A61H 23/008
See application file for complete search history.

(56) References Cited

U.S. PATENT DOCUMENTS

| | | |
|---|---|---|
| 2005/0033201 A1* | 2/2005 | Takahashi ...... A61B 17/320068 601/2 |
| 2007/0038160 A1 | 2/2007 | Tanaka et al. |
| 2011/0089248 A1 | 4/2011 | Deng et al. |
| 2011/0208206 A1* | 8/2011 | Diamant .......... A61B 17/22022 606/128 |

OTHER PUBLICATIONS

International Preliminary Report on Patentability dated Dec. 10, 2019 re: Application No. PCT/EP2019/051279, pp. 1-8, citing: US 2007038160 A1, US 2011/208206 A1 and US 2011/089248 A1.

* cited by examiner

SYSTEM FOR CRUSHING AND/OR REMOVING BODY STONES, METHOD FOR PROVIDING SUCH A SYSTEM AND ADAPTER ELEMENT

TECHNICAL FIELD

The present disclosure concerns a system for breaking up and/or removing body stones, a method for providing such a system and an adapter element.

BACKGROUND

Systems are known for breaking up body stones, such as urinary stones or kidney stones, with which they can be broken up or crushed and then the resulting fragments of body stones can be removed. In particular, these are so-called intracorporeal lithotripters, in which an instrument is endoscopically introduced up to the stone in order to break it up. Well known are optical systems with a laser as source, electro-hydraulic spark discharge devices and continuously or pulse-like excited probes which crush the stones mechanically. In the case of mechanical systems, an essential component includes a source that causes shock waves and/or vibrations and a probe that is detachably connected to the source. Typically, the essentially needle-shaped or rod-shaped or hollow cylindrical probe is aligned with a first proximal end to the body stone to be destroyed, while the shock wave and/or vibrations emanating from the source are transmitted to the probe via a second distal end opposite the first end. The probe then guides or transmits the shock wave and/or sound wave introduced at the second end to its area of application in the vicinity of the body stone and then destroys it by the resulting mechanical movement of the proximal probe tip.

Due to the high mechanical loads occurring during operation, in particular due to the probes which frequently vibrate in the ultrasound range, these must be replaced after a limited number of uses. For this reason, the probes are usually detachably connected to the source via an interface and can thus be replaced regularly. Furthermore, a coupling mechanism found in the interface area allows different types of probes to be connected to the same source.

From the US 2011/0 208 206 A1 a system is known in which an RFID transmitter is embedded in the probe. Using the probe, information about the probe can be transmitted via wireless communication for its identification. However, it has been found that due to the intensive exposure to ultrasound vibrations and the high temperatures and aggressive chemicals due to sterilization, the functionality of the RFID transmitter is adversely affected, especially in the long term.

SUMMARY

Based on this background, the present disclosure provides a system for breaking up and/or removing body stones, with which the functionality of the RFID element can be ensured, in particular after the probe has been connected to the source several times, i.e. permanently.

This is achieved by providing a system according to claim 1, by an adapter element according to claim 9 and a method according to claim 10. Further advantages and features of the disclosure result from the subclaims as well as the description and the attached figure.

The disclosure provides a system for breaking up and/or removing body stones, comprising a source causing shock waves and/or ultrasound waves, and
a probe, wherein the source and the probe can be reversibly connected via an interface for transmitting the shock waves and/or ultrasound waves to the probe, and the probe comprises an ident element for identifying the probe and/or for storing data, wherein the ident element is arranged in or on the probe so as to be protected against vibration and/or temperature.

The identification element is preferably an RFID element, but can also be another electrical or electromagnetic element. In the following, an RFID element is preferably mentioned, without limiting the embodiments to such an element.

Compared to the systems known from the state of the art, the system according to the disclosure proves to be advantageous in particular because the ident or RFID element is less affected by the ultrasound vibrations. Protected from vibrations means, in particular, that the vibrations generated during operation, in particular ultrasound vibrations, are only partially, i.e. only in part, transmitted to the RFID element. In particular, it can be used as a reference that with the system according to the disclosure the (absorbed) vibrations of the RFID element are reduced compared to a system in which the RFID element is rigidly connected to the probe. The RFID element is thus preferably decoupled from the probe, in particular vibrationally decoupled from the probe. For example, it is intended that the RFID element for a vibration-protected arrangement is loosely or indirectly connected to the probe or arranged on the probe via an attenuator.

Basically, an Ident element is a component that can be used for the automatic and contactless identification or localisation of objects. In particular, the ident Element comprises a transponder in which information about the respective probe is stored. Coupling with the ident element is effected by means of a reader that generates an alternating magnetic field with a comparatively short range or high-frequency radio waves. This not only transmits data, but also supplies the transponder with energy. To achieve longer ranges, it is conceivable to equip the ident element with its own power supply or an electromagnetic interface.

Furthermore, it is intended that the interface has an appropriate coupling mechanism for the detachable connection of the source and the probe. In particular, the coupling mechanism comprises a source-side component and a probe-side component which are designed to be complementary to one another and thus preferably form a positive and/or non-positive connection with one another in the connected state. For example, the coupling mechanism is a thread with an internal and external thread as source-side and probe-side components or a bayonet cap. Preferably, the ident or RFID element includes a memory device in which information about the probe can be stored. For example, information on the manufacturer, a dimensioning of the probe, number of inserts of the probe or similar information is stored in the memory device. This can be an advantage in preventing the system from being used improperly, for example because of an unsuitable or used-up probe. Preferably, the storage device can be overwritten, i.e. information stored in the storage device can be updated.

In particular, the system is an intracorporal lithotripter, in which the probe is preferably substantially needle-shaped, rod-shaped or hollow cylindrical, i.e. the probe has a circular cross-section substantially in a plane perpendicular to its longitudinal direction and extends, viewed in its longitudinal direction, many times further than its diameter measured in the cross-sectional plane. In the operational state, i.e. in a state in which the probe is connected to the source, a first proximal end of the probe faces away from the source and the second distal end, opposite the first end, faces the source. This allows the shock waves or sound waves to be transmitted along a central direction from the source to the second end of the probe and from the second end to the first end. To break the stone, the first end is then placed directly on the stone.

The probe is preferably formed hollow. This makes it advantageously possible to provide a hollow area through which shredded parts or debris can be removed from the first end to the second end, e.g. by suction. Furthermore, it is preferably intended that the probe can be detachably connected to a hand-held device in which the source is integrated. Preferably, the probe is connected to one end of the hand-held device. The hand-held device preferably comprises a grip area and a projectile area. In the projectile area, the source preferably has a first partial source for inducing a shock wave by means of a projectile and a second partial source for inducing a sound wave by means of piezoelectric elements, which accordingly introduce a shock wave and/or a sound wave into the probe. By means of the grip area, the probe can preferably be aligned or a user can align or position the first end via the grip area.

Furthermore, it is intended that the probe has a hollow body which essentially determines the needle-like shape of the probe and an adapter element at its second distal end for connecting the probe to the source. In the operational state, a first recess of the adapter element is directed towards the source such that the projectile can engage in the first recess. The adapter element and/or the hollow body is in particular made of a metal, for example a stainless-steel comprising chromium and/or nickel.

According to a preferred embodiment of the present disclosure, it is intended that the RFID element is integrated into a ring element, in particular a ring element made of plastic, and/or the probe has a metal tube. By means of the ring element, the RFID element can advantageously be mounted advantageously on the probe easily in a vibration-protected manner. The thermal conductivity of plastics is also generally lower than that of metal, so that the RFID element is protected from the high temperatures of steam sterilization. Preferably, the ring element encases the probe when mounted. In particular, the ring element encases the adapter element, for example at the level of the first recess when viewed in the central direction. Furthermore, it is intended that the ring element has an omission to accommodate the RFID element. The RFID element can be placed in this omission and preferably connected to the ring element with a material bond. When mounted on the probe, an opening on the ring element side, through which the RFID element is inserted into the omission, faces the source. In other words, the RFID element is located on the side of the ring element facing the source when mounted. With the probe, which is designed as a metal tube, it is advantageously possible to aspirate body stone fragments.

It is also conceivable that the RFID element is oriented in such a way that its signal strength is maximum in a direction away from the first end of the probe. Furthermore, it is provided that the ring element, viewed in a radial direction relative to the central axis, protrudes from an outermost edge of the probe, in particular the adapter element. This makes it possible that the RFID element is not covered by the metallic probe, in particular a collar on the adapter element. This also contributes to ensuring the functionality of the RFID element.

Preferably, the RFID element embedded in the ring element has a square cross-section and is smaller than 5×5 mm, preferably smaller than 4×4 mm and more preferably smaller than 3×3 mm. With such a small dimensioned cross-section, for example 2.7×2.7 mm, a comparatively small RFID element is integrated into the ring element with advantage.

Furthermore, it is conceivable that the ring element may include a visually detectable marking, for example a specific colour, a specific external contour (e.g. round, octagonal, nine-cornered . . . ) and/or a bar or QR code. This makes it easy for the user to identify the type of probe without using the RFID element. For example, a specific colour can be defined for each probe type. The individual probe types differ, for example, in terms of their intended use, dimensioning, e.g. with regard to the length of the hollow body and/or the diameter.

In a further embodiment of the present disclosure, it is provided that the ring element can be mounted on the probe with play, forming a gap, wherein a gap width of the gap preferably assumes a value between 0.05 mm and 0.2 mm, more preferably a value between 0.08 mm and 0.13 mm and most preferably a value of substantially 0.1 mm. The gap is advantageously used to prevent the ring element from resting firmly against the probe, in particular the adapter element. The result is a sufficient decoupling from the vibrations of the probe during operation. Especially for a gap width of 0.1 mm, it has been found to be advantageous that not only can a sufficient end coupling be realized, but also that the ring element is arranged on the probe in such a way that it does not rattle or even come loose during operation. In particular, play means that the ring element can be easily twisted with the finger when mounted. In particular, a gap is formed that extends radially between the probe and the ring element in relation to the central direction.

It is preferable that a gap dimension or gap width is at least dimensioned so that it is larger than the movements of the ring element caused by the vibrations. In this way a sufficient decoupling can be guaranteed. For example, the movements of the probe in the area of the ring element induced by the vibrations have an amplitude below 0.1 mm.

Preferably the probe and the source are connectable by means of an adapter element, wherein the ring element is connectable for axial securing between a collar of the adapter element and a projection of the adapter element. This has the advantage of preventing the ring element from shifting in the axial direction and thus becoming detached from the probe. In particular, the projection is dimensioned in such a way that the ring element can be pulled over the projection when it is mounted.

It is intended that the system should comprise a control device, the control device setting parameters at the ultrasound source depending on information transmitted by the RFID element. For example, the control device is integrated into a desktop device and comprises a reader or receiver that receives the signals from the RFID element. The control device can then use the received information to automatically set the parameters optimized for the respective probe type for the first and/or second partial source. In addition, it is conceivable that the control device will stop the operation of the system if the connected probe is not compatible with the source or its lifetime (1-way probe, 5-way probe) has been exceeded.

Preferably, the system is configured in such a way that time-varying status information is transmitted by means of the RFID element. For example, the time-varying status information is the number of possible uses of the probe. For this purpose, it is intended that after each use of the probe, the information about the number of possible uses is reduced by one. This has the advantage of ensuring that the probe is not used too often, otherwise it will break. Preferably, the control device or a transmitter in the control device is designed to change or overwrite information stored in the RFID element. In particular, the control device is configured in such a way that operation of the system is inhibited if the number of possible uses has dropped to zero. This has the advantage of preventing improper use of the probe and possibly injury to the patient.

It is particularly preferred that the source is integrated in a hand-held device and preferably a transmitter, in particular an annular antenna, for the RFID element is embedded in the hand-held device. In particular, the transmitter comprises a reader and an antenna with which the transmitter can communicate with the RFID element on the one hand and with the control device for providing and overwriting information stored in the memory device of the RFID element on the other hand. In other words, part of the RFID transmitter is transferred to the handset and is ready to function, for example, when connected to the RFID element. The transmitter can exchange information with the RDIF element via a cable, especially a coaxial cable. By outsourcing the communication interface for the RDIF element into the hand-held device, it is possible to dispense with the corresponding components in or on the probe and to optimize the placement for the most interference-free transmission of wireless signals. For example, in the assembled state of source and probe, the ring-shaped antenna is aligned parallel to the ring element, preferably concentric to the ring element. Furthermore, it is conceivable that the antenna on the side of the hand-held device, in particular the ring-shaped antenna, could be positioned in an area of the hand-held device facing the probe in the assembled state.

It is advantageous if the ring element is made of a sterilizable material, in particular polyphenylene sulfone (PPSU). Under a sterilizable material is to be understood in particular one that can be sterilized by means of a sterilization process, preferably with the same sterilization process with which the probe is sterilized without the ring element being substantially modified by the sterilization process. Sterilisation makes it possible to use the ring element for intracorporal lithotripsy, for example. It is conceivable that the ring element is sterilized together with the probe.

The present disclosure further provides an adapter element for a system for breaking up and/or removing body stones, in particular for a system according to the disclosure, wherein by means of the adapter element a probe and a source can be connected to each other via a thread, wherein the thread has a plastic region, wherein the plastic region is preferably realized by a plastic coating and/or an insert. All features described for the system according to the disclosure and their advantages can also be transferred to the adapter element and vice versa.

Compared to the adapter elements known from the state of the art, the fitting of the thread with a plastic region according to the disclosure proves to be advantageous in that a connection between the source and the probe that is more stable against vibrations can be realized without having to tighten the interlocking threads of the source and probe too tightly. Excessive tightening of this kind carries the risk that the two interlocking threads will be welded together by the ultrasound movement during operation and the system will be irreversibly damaged. For this reason, the probe and the source are preferably tightened together via their threads to a specified torque. The plastic region being designed on the adapter element side has proven to be particularly advantageous, since each time the probe and source are connected via the thread, an inhibiting effect caused by the plastic region is reduced. In particular, it is intended that the probe has an internal thread for connection and that the source or a hand-held device in which the source is integrated provides a complementary external thread.

It is preferable that the plastic region is dimensioned or designed to provide an inhibiting effect for a certain number of connections, the number being preferably matched to the possible number of potential uses for the probe. It is also conceivable that the plastic region does not extend over the entire length of the thread. This makes it possible in an advantageous way that the external and internal threads can be screwed together at least partially with ease, in particular as long as the external thread and the internal thread interlock in an area outside the plastic region. For example, the plastic region is realized by a coating, in particular single threads. However, it is also conceivable that a plastic insert is embedded in the adapter element in such a way that it projects into the receiving area or interior space defined by the general course of the internal thread of the adapter element. When the external thread of the source is first connected to the probe, a thread is then cut or formed into the insert.

According to another aspect of the present disclosure, a method is provided for providing a system for breaking up and/or removing body stones, in particular a system according to the disclosure, wherein the probe and the source are connected to each other, preferably wherein the probe and the source are screwed together with a fixed torque and/or signals are emitted from an RFID element. All features described for the system according to the disclosure and their advantages can also be transferred to the method and vice versa. Preferably, the probe and the source are screwed together using a torque wrench.

BRIEF DESCRIPTION OF THE DRAWINGS

Further advantages and features result from the following description of preferred embodiments of the subject matter of the disclosure with reference to the attached figures. Individual features of the individual embodiments can be combined within the scope of the disclosure.

It is shown in.

DETAILED DESCRIPTION OF THE DRAWINGS

Figure 1:
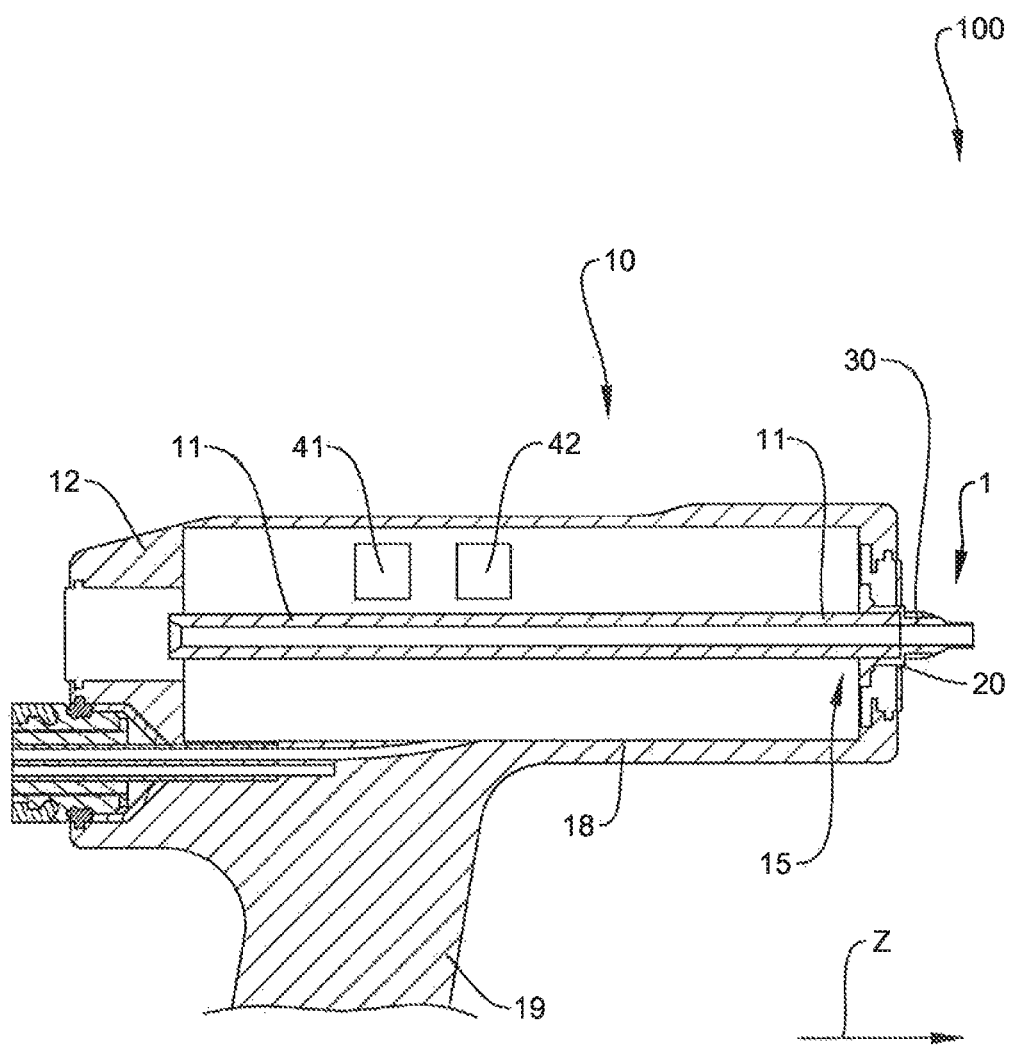
FIG. 1: a system for breaking up and/or removing body stones according to a first preferred embodiment of the present disclosure.

FIG. 1 schematically illustrates a system 100 for breaking up and/or removing body stones. For example, body stones are kidney stones or urinary stones that can be broken up using the system 100. Essential components of such a system 100 are a source 10 inducing shock waves and/or ultrasound waves and a probe 1. In particular, it is provided that the shock waves and/or ultrasound waves emitted by the source 10 are transmitted to the probe 1, whereby a first proximal end 21 of the probe 1 which is turned away from the source 10 and which is facing the body stone during operation causes a breaking up of the body stone or of parts of the body stone.

For the transmission of shock waves and/or ultrasound waves, the source 10 and the probe 1 are detachably connected to each other via an interface 15. In the embodiment shown in FIG. 1, it is provided that the source 10 is integrated into a hand-held device 12, in particular with a projectile area 18 and a grip area 19, and a projectile 11 is provided for transmitting the shock waves and piezo elements in the projectile area 18 are provided for transmitting the ultrasound waves, the projectile 11 being driven by means of a first partial source 41 to perform an impact movement and the probe 1 being driven by means of a second partial source 42 to perform an ultrasound movement. In the ready-for-operation state, the projectile 11 and a second distal end 22 of the probe 1 facing the projectile 11 are arranged in alignment with one another and the projectile 11 acts on the second end 22 of the probe 1, preferably striking or hammering, to transmit the shock waves. The second partial source 42 comprises piezoelectric elements, which are arranged in a ring around the projectile channel and directly couple ultrasound waves into the probe at the interface 15. It has proven to be particularly advantageous if the shock waves are superimposed by the ultrasound waves, which are preferably higher-frequency than the shock waves.

Figure 2A:
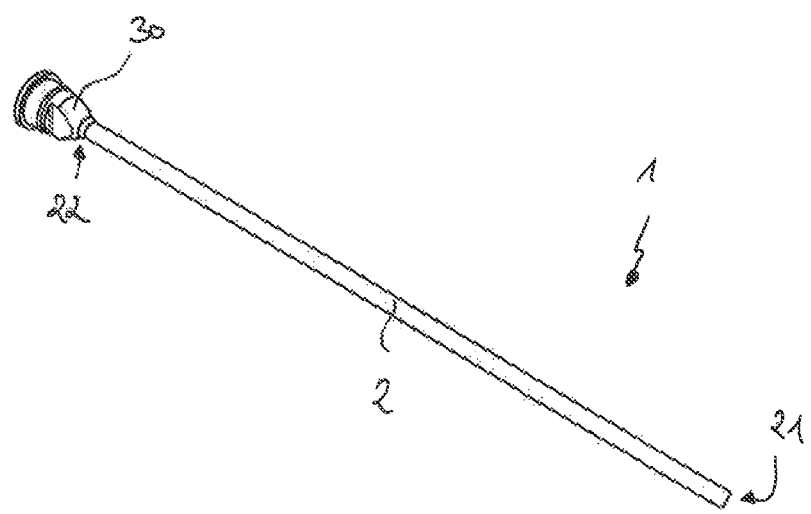
FIGS. 2 and 2b: probe for a system according to the first preferred embodiment.
Figure 2B:
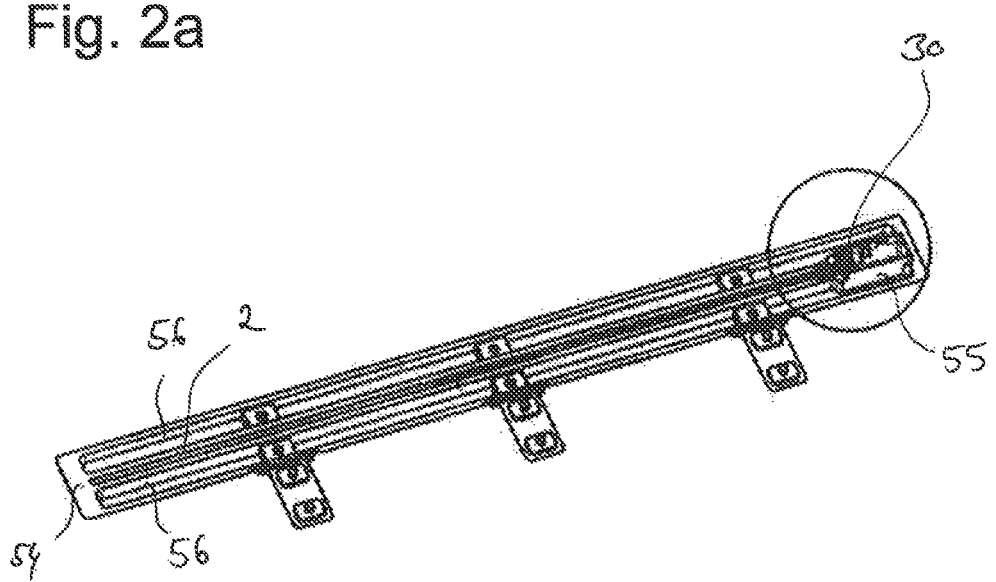

Furthermore, it is intended that probe 1 is needle-shaped, as shown in FIG. 2a. FIG. 2b shows the probe 1 in a packed state, preferably sterile packed. It is advantageous for the needle-shaped probe 1 to pick up the shock and/or sound waves applied to probe 1 at the second end 22 and transmit them to the first end 21 of probe 1. The first end 21 of the probe 1, which is placed on the body stone, then causes the body stone to be broken-up during operation. In addition, it is advantageous that the needle-shaped probe 1 is hollow in order to suck off or remove the broken or crushed parts of the body stones via the probe 1, in particular the hollow area 25 in the probe 1 provided for this purpose. For this purpose, for example, a negative pressure is generated in the hand-held device 12, which causes the corresponding suction.

Furthermore, it is intended that the probe 1 has a hollow body 2 which essentially determines the needle shape and an adapter element 30 at its second end 22. In the packaged state shown in FIG. 2b, the adapter element 30 is mounted in a casing-like protective body 55 and the hollow body 2 is mounted between two protective webs 56. The probe 1 is placed on a support 54 and is preferably enclosed or sheathed in a cover, in particular a plastic cover.

Figure 5:
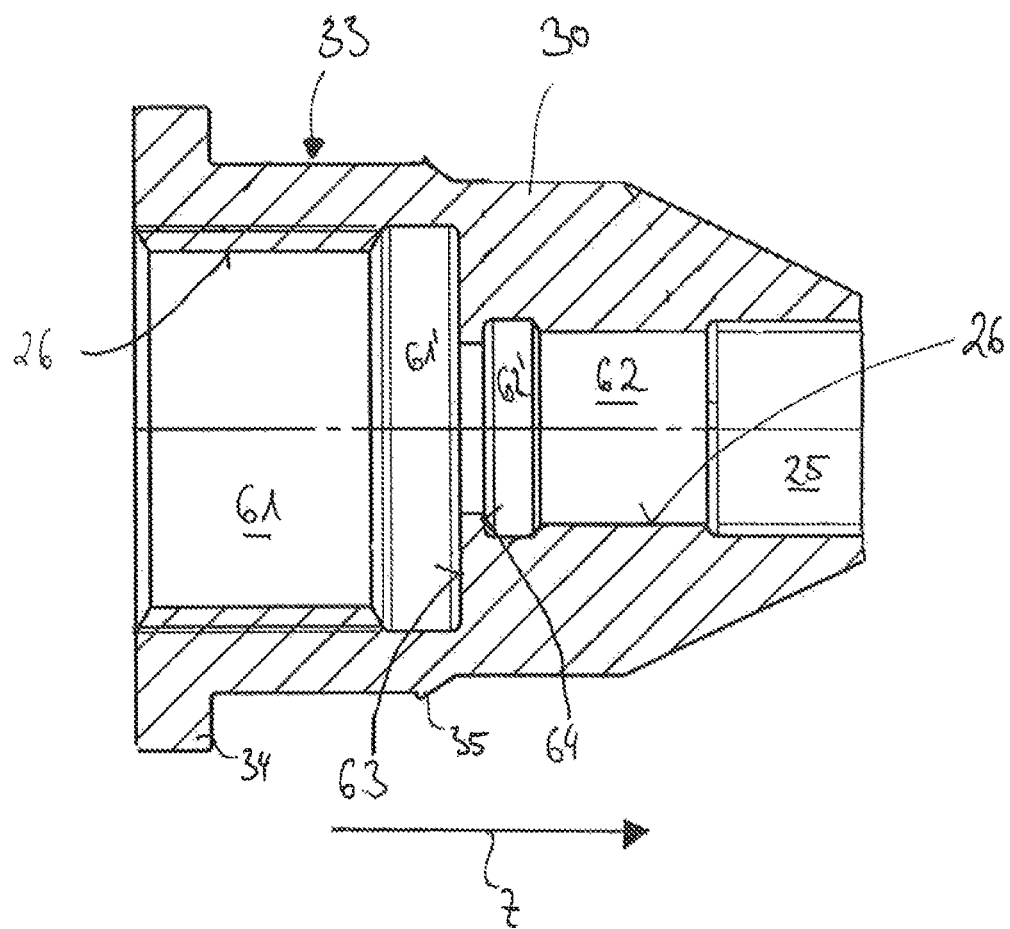

FIG. 5 shows the adapter element 30 schematically in a sectional view. The adapter element 30 is designed in the shape of a sleeve, wherein a course of an inner side 26 of the adapter element 30 is stepped when viewed in a central direction Z. The central direction Z is essentially parallel to a direction along the direction of the sound waves and/or shock waves transmitted to probe 1. Due to the stepped course on the inside 26 of the adapter element 30, a first recess 61 and a second recess 62 are preferably formed opposite each other. During operation, the projectile 11 hits the first recess 61 and the hollow body 2, which essentially determines the needle shape, is arranged within the second recess 62. The first recess 61 is bounded in the central direction Z by a first end surface 63 and the second recess 62 in the opposite direction by a second end surface 64. With the first end surface 63, the stepped course tapers on the inner side 26, seen in the central direction Z, in such a way that an inner diameter in this area is smaller than the outer diameter of the projectile 11, while with the second end surface 64 the stepped course tapers in such a way that the inner diameter in this area is smaller than an outer diameter of the hollow body 2. It is provided that, viewed in the central direction Z, the first recess 61 extends over a first length L1 and the second recess 62 extends over a second length L2, the ratio between the first length L1 and the second length L2 assuming a value between 0.75 and 0.9, preferably between 0.78 and 0.85 and more preferably between 0.79 and 0.82. Furthermore, it is provided that, viewed in the central direction Z, a cross-section extending perpendicularly to the central direction Z is partially widened in a first partial region 61' of the first recess 61 or second partial region 62' of the second recess 62 adjacent to the first or second end surface, in particular is larger than an outside diameter of the projectile 11 or of the hollow body 2.

Furthermore, it is intended that the probe 1, preferably also the adapter element 30, is made of a metal, especially a stainless steel. In addition, the adapter element 30 comprises a further gripping area 31 on its outside, for example in the form of two with respect to each other parallel or slightly inclined flat surfaces 38.

The probes 1 are a wear item that can no longer be used after a limited number of uses. For this reason, the source 10 and the probe 1 are designed in such a way that they can be detachably connected or exchanged, i.e. they are reversibly connectable. This also makes it possible to use different types of probes with the same source 10.

To prevent improper use of the probes 1, it is intended that the probe 1 includes an ident or RFID element 5. By means of the RFID element 5. It is advantageous to be able to identify the Probe 1 connected to the source 10, particularly with regard to its status and/or probe type. This makes it possible to prevent the System 10 from being operated with an unsuitable probe type. Furthermore, it is preferably intended that parameters for the operation of the source, in particular of the first partial source 41 and/or the partial source 42, are adapted to the respective currently used probe type. For this purpose, the RFID element 5 communicates with a control device, which is, for example, integrated in a table unit, and transmits the required information about the probe type currently connected to the source 10 to the control device. Preferably, the desired parameters are then set or a user can select from a list of preferred parameters for the probe type. It is also intended that a transmitter, for example an antenna and/or a reader, is integrated in the hand-held device 12, wherein when the system 100 is operational (i.e. when the probe 1 and source 10 are connected) the transmitter is in a communication link with the RFID element 5, for example via a cable, in particular a coaxial cable.

Figure 3A:
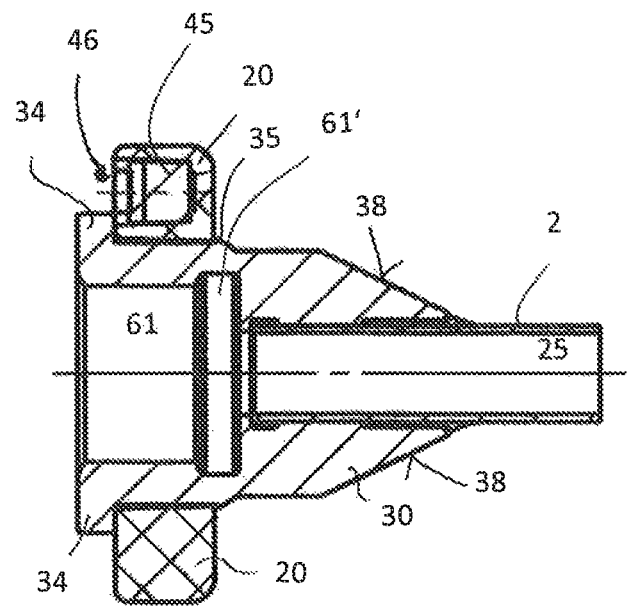
FIGS. 3a and 3b: detailed view of an adapter element with a ring element for a system of the preferred embodiment of the present disclosure, in a sectional view (3a) and a top view (3b)
Figure 3B:
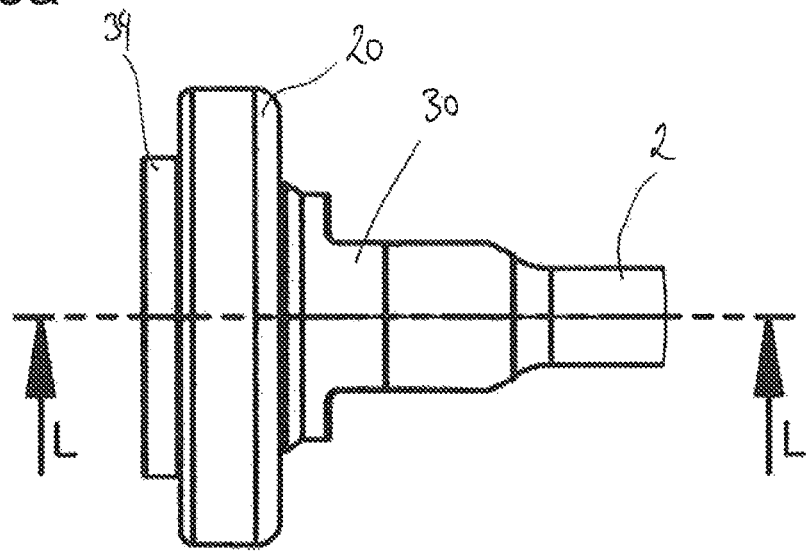
Figure 4:
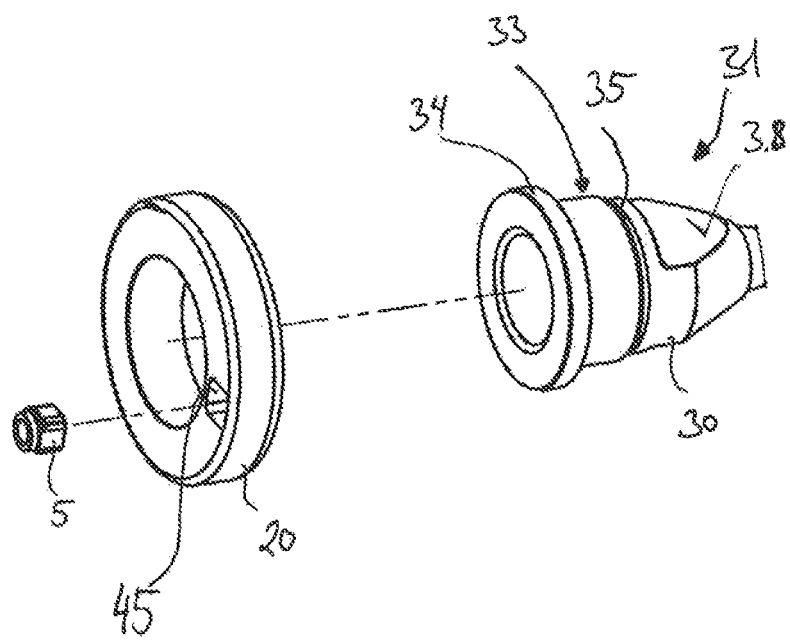
FIG. 4: exploded view of the detailed view from FIGS. 3a and 3b, FIG. 5: an adapter element of the probe from FIGS. 2 to 4, FIG. 6: a ring element for the probe from FIGS. 2 to 5, and FIG. 7. an adapter element for a probe according to a second preferred embodiment of the present disclosure.

However, the ultrasound vibrations acting on the RFID element 5 and the material of the probe 1 impair the functionality of the RFID element 5. In order to improve the functionality of the probe 1 during operation, it is advantageous to place the RFID element 5 on the probe 1 so that it is protected against vibration. For this purpose, the RFID element 5 is preferably integrated into a ring element 20, in particular into a ring element 20 made of plastic. The ring element 20 is in turn mounted on the probe 1, especially on an outside of the probe and preferably in a connection area 33 to an outside of the adapter element 30. FIGS. 3a and 3b show the adapter element 30 with mounted ring element 20 in a sectional view (FIG. 3a) and a top view (FIG. 3b) and FIG. 4 shows an exploded view of adapter element 30, ring element 20 and RFID element 5.

The ring element 20 is preferably mounted to the probe 1 with play in such a way that the transmission of ultrasound vibrations to the ring element 20 is reduced and at the same time the ring element 20 has a sufficiently tight fit to the probe 1. The ring element 20 is in such a state with play, for example, if the ring element 20 can be easily turned with the fingers. Furthermore, it is intended that the material from which the ring element 20 is made can be sterilized. Polyphenylene sulfone (PPSU) has proven to be a particularly advantageous material for this purpose.

In the embodiment shown, the ring element 20 is arranged on the adapter element 30, in particular at the level of the first recess 61 when viewed in the central direction Z. To support the ring element 20, the adapter element 30 has a circumferential collar 34 at its end facing the probe of the source when mounted. This collar 34 forms a stop for the ring element 20. Seen in the central direction Z, a projection 35 or a nose is provided on the outside of the adapter element, offset from the collar 34. The ring element 20 is preferably arranged between the projection 35 and the collar 34 for axial securing, i.e. to prevent the ring element 20 from slipping in the axial direction (parallel to the central direction).

Figure 6:
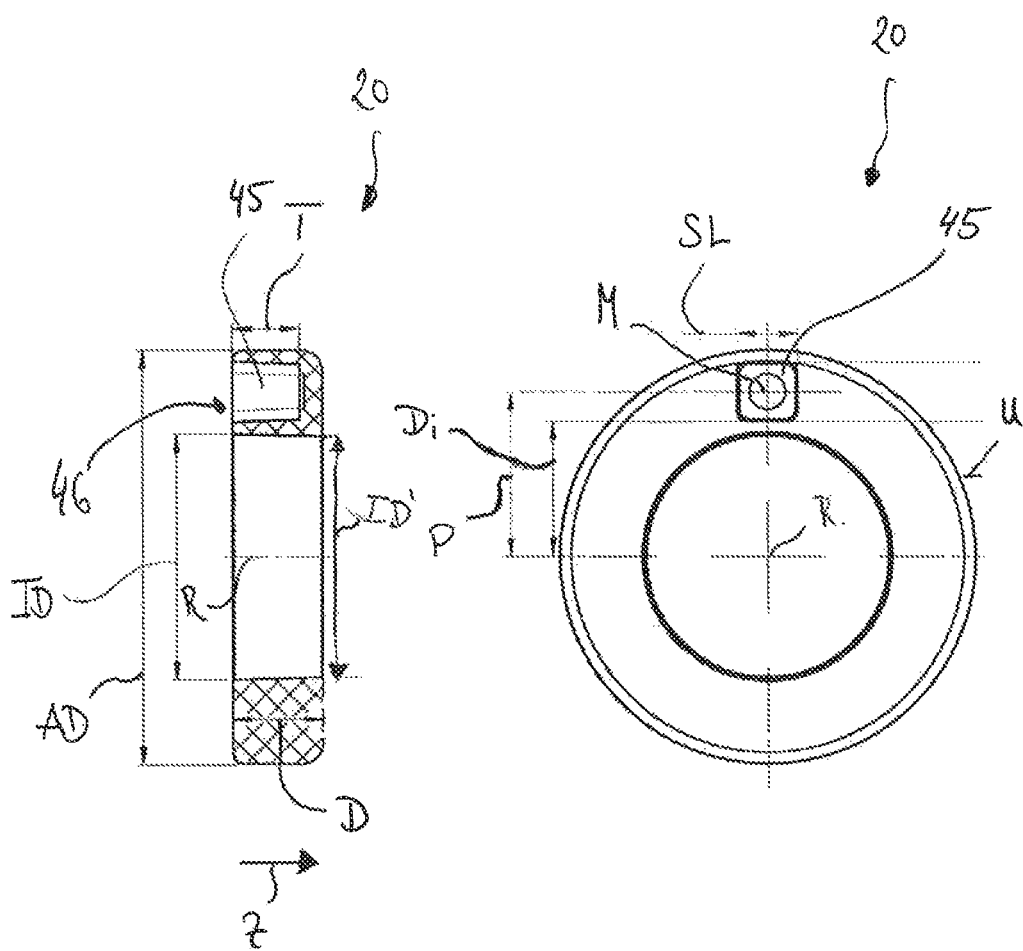

FIG. 6 shows in detail the ring element 20 with an inner diameter ID and an outer diameter AD. For example, the outer diameter AD assumes a value between 15 and 20 mm, preferably of essentially 18.6 mm, while the inner diameter assumes a value between 10 and 13 mm, preferably of 11 mm. Furthermore, it is conceivable that the inner diameter ID, viewed in a direction parallel to the axis of rotational symmetry R, to which the outer circumference U of the ring element 20 is preferably completely rotationally symmetrical, becomes smaller, in particular steadily smaller. For example, the inner diameter ID has 11 mm at one end face of the ring element and a further inner diameter ID' of 10.8 mm at the opposite end face of the ring element 20.

An omission 45 is provided to accommodate the RFID element 5. Relative to the axis of rotational symmetry R, the omission 45 starts at a distance Di, seen in the radial direction, and is arranged with its centre M away from the axis of rotational symmetry R by a positional distance P. The positioning distance P is preferably dimensioned so that the omission 45, viewed in the radial direction, is located centrally between the inner diameter ID and the outer diameter AD. In particular, the ring element 5 is aligned in the mounted state in such a way that an opening 46 on the ring element side, via which the RFID element 5 can be inserted into the omission 45, faces the collar 34 of the adapter element 30 or the source 1. Furthermore, a ratio between a depth T of the omission 45 measured in the central direction Z and a thickness D of the ring element 20 measured in the same direction assumes a value between 0.75 and 0.98, preferably between 0.8 and 0.95 and more preferably between 0.85 and 0.94. It is further provided that in the assembled state, viewed in the radial direction with respect to the central direction Z, the ring element 20, in particular its outer circumference U, protrudes with respect to the collar 34 of the adapter element 30. In particular, the ring element 20 protrudes to such an extent that the opening 46 of the omission 45 or part of the omission 45 is exposed (see FIG. 3a). Preferably, the omission 45 is covered by the collar 34 by less than 20%, preferably less than 15% and more preferably less than 10%. Therefore, the RFID element 5, which is embedded in the ring element 20, advantageously remains accessible or reliable communication with the RFID element 5 for information exchange can be ensured.

To fix the RFID element 5 in the omission 5, a material-locking connection is provided, for example by means of an adhesive. In doing so, the omission 5 is preferably only to be filled partially or partially filled with the adhesive. It is also intended that the omission is square, in particular with a side length SL. Furthermore, it is preferably provided that a ratio of the thickness D of the ring element 20 to the first length L1 assumes a value between 0.5 and 0.9, preferably between 0.55 and 0.8 and particularly preferably between 0.63 and 0.73.

The connection of the probe 1 to the source 10 is preferably made via a thread 71, e.g. the adapter element 30, especially seen in central direction Z at the level of the collar 34, has an internal thread on its inner side 26. When screwing the adapter element 30 to the source 10, care must be taken that the adapter element 30 is not overtightened, otherwise the vibrations occurring during operation will connect the adapter element 30 to the source 10, especially its thread, and thus destroy the source 10 or the hand-held device 12. It has therefore proved to be advantageous to connect the probe 1 to the source 10 in a controlled manner at a fixed torque, preferably by means of a torque wrench.

In order to counteract loosening of the adapter element 30 from the probe 1 due to the vibrations occurring during operation, despite the required reduced torque with which the probe 1 is connected to the source 10, it is provided in the embodiment shown that the thread 71 is coated, in particular with a plastic coating. Preferably only individual threads or all threads of thread 71 are covered with the plastic coating. In particular, only those threads are coated in which the mating thread or external thread on the hand-held device side last engages during connection. This facilitates the initial screwing on with advantage and the coating on the last threads stabilizes the detachable connection between the probe 1 and the source 10. For example, only the last two threads are coated with the plastic coating. Preferably, the ratio of the number of threads with coatings to the number of threads without coating takes a value less than 1, preferably less than 0.5 and more preferably less than 0.25. It has been shown to be advantageous that the plastic coating wears off when the probe 1 is repeatedly fitted and removed. In particular, the plastic coating is designed, for example by suitable selection of the material, the number of coated threads and/or the coating thickness, in such a way that the number of possible screw-on operations can be determined. In particular, this number of possible screw-on operations is coordinated with the maximum number of possible uses for probe 1.

Figure 7:
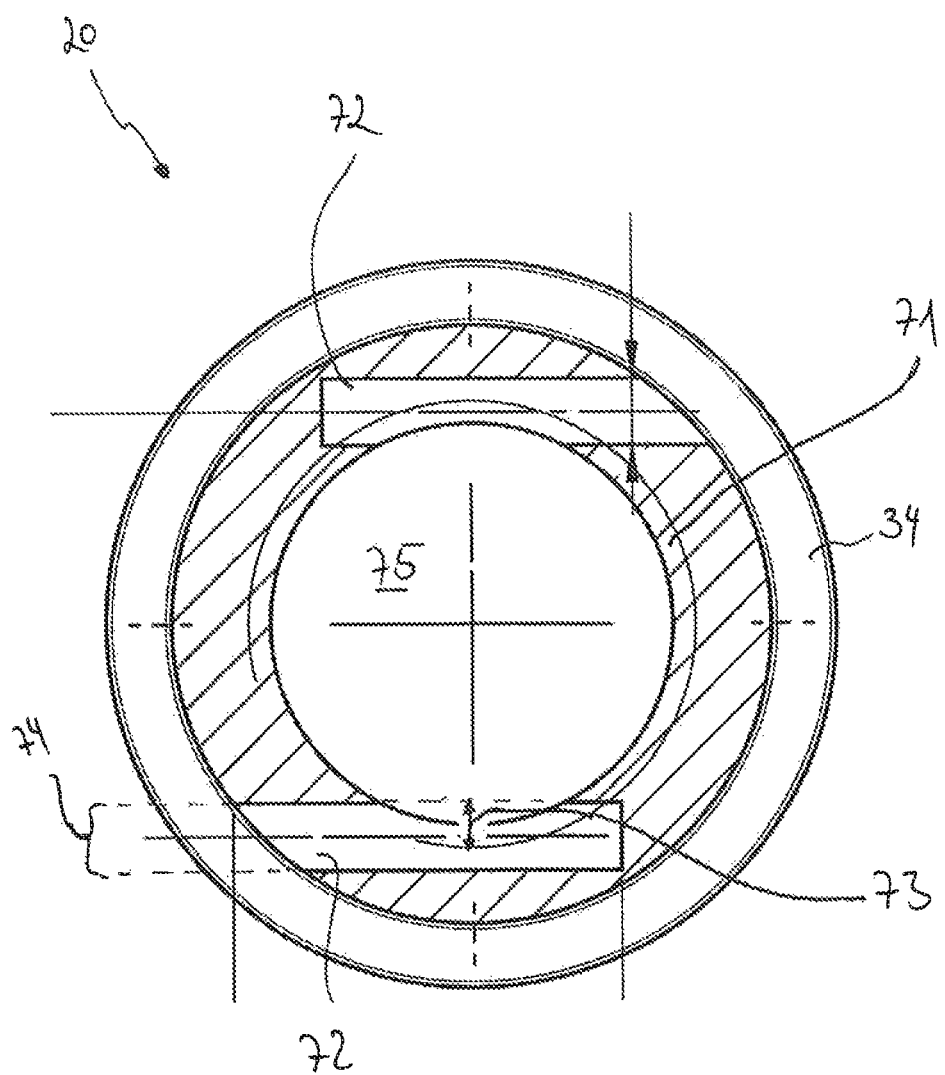

FIG. 7 shows an adapter element 30 for a System 1 according to a second preferred embodiment of the present disclosure. In this respect, the adapter element 30 differs from that shown in FIG. 5 essentially only with respect to the thread 71 with which the probe 1 is connected to the source 10. Instead of coating individual threads, it is intended here that one or more pin-like inserts 72, preferably plastic inserts, are embedded in the adapter element 30. In particular, in this case the adapter element 30 is provided with a bore, which preferably runs tangentially to the internal thread and into which the pin-type insert 72, preferably a plastic insert, can be inserted. In an inserted or pushed-in state, the insert 72 protrudes into an inner space 75 of the adapter element 30 before the first connection with the source 1, or protrudes inwards in relation to the thread 71 in the radial direction. By selecting a suitable material for the insert 72, it is then possible that when the probe 1 is first connected to the source 10, the thread of the source, in particular an external thread of the source, cuts a thread into the insert 72 embedded in the adapter element. It has been found to be advantageous that the insert 72 inhibits the thread of the source 10 and thus effectively prevents loosening of the connection between the source 10 and the probe 1 during operation. Preferably, the probe 1 with the insert(s) can be screwed on up to five times.

If two inserts 72 are provided, they are aligned essentially parallel to each other. Furthermore, it is provided that the insert is dimensioned in such a way that in the screwed-on state, viewed in the radial direction, a section 73 cut to form part of the thread is larger than a width 74 of the pin-like insert 72. In particular, a ratio of the section 73 belonging to the thread to the width of the insert 72 assumes a value between 0.3 and 0.75, preferably between 0.4 and 0.6 and more preferably between 0.45 and 0.55.

The invention claimed is:

1. A system for breaking up and/or removing body stones, comprising:
   a source causing shock waves and/or ultrasound waves, and
   a probe,
   wherein the source and the probe can be reversibly connected via an interface for transmitting the shock waves and/or ultrasound waves to the probe and the probe comprises an ident element for identifying the probe,
   wherein the ident element is arranged in or on the probe so as to be protected against vibration,
   wherein the ident element is integrated in a ring element made of plastic.

2. The system according to claim 1, wherein the ring element can be mounted on the probe with play, forming a gap, wherein a gap width of the gap assumes a value between 0.05 mm and 0.2 mm.

3. The system according to claim 1, wherein the probe and the source are connectable by means of an adapter element, wherein the ring element is connectable for axial securing between a collar of the adapter element and a projection of the adapter element.

4. The system according to claim 1, the system comprising a control device, the control device setting parameters at the source, depending on information transmitted by the ident element.

5. The system according to claim 1, wherein the system is configured such that time-varying status information is transmitted by means of the ident element.

6. The system according to claim 1, wherein the source is integrated in a hand-held device and a transmitter, for the ident element is embedded in the hand-held device.

7. The system according to claim 1, wherein the ring element is made of a sterilizable material.

8. An adapter element for a system for breaking up and/or removing body stones, according to claim 1, wherein by means of the adapter element the probe and the source can be connected to each other via a thread, wherein the thread has a plastic region and wherein the plastic region is realized by a plastic coating and/or by an insert.

9. A method for providing a system for breaking up and/or removing body stones, according to claim 1, wherein the probe and the source are connected to each other and wherein the probe and the source are screwed together with a fixed torque and/or signals are emitted from the ident element.

* * * * *